United States Patent
Nedohin et al.

(10) Patent No.: US 10,272,359 B2
(45) Date of Patent: Apr. 30, 2019

(54) REACTOR EFFLUENT WASH TO REMOVE AROMATICS

(71) Applicant: UOP LLC, Des Plaines, IL (US)

(72) Inventors: Gregory J. Nedohin, Des Plaines, IL (US); Mike Banach, North Barrington, IL (US); David N. Myers, Hoffman Estates, IL (US)

(73) Assignee: UOP LLC, Des Plaines, IL (US)

( * ) Notice: Subject to any disclaimer, the term of this patent is extended or adjusted under 35 U.S.C. 154(b) by 11 days.

(21) Appl. No.: 15/796,718

(22) Filed: Oct. 27, 2017

(65) Prior Publication Data

US 2018/0043280 A1  Feb. 15, 2018

Related U.S. Application Data

(63) Continuation of application No. PCT/US2016/058870, filed on Oct. 26, 2016.

(60) Provisional application No. 62/252,160, filed on Nov. 6, 2015.

(51) Int. Cl.
| | |
|---|---|
| *C07C 5/32* | (2006.01) |
| *B01D 5/00* | (2006.01) |
| *B01D 1/28* | (2006.01) |
| *C07C 5/327* | (2006.01) |
| *C07C 7/00* | (2006.01) |
| *C07C 7/09* | (2006.01) |

(52) U.S. Cl.
CPC ........... *B01D 5/003* (2013.01); *B01D 1/2846* (2013.01); *C07C 5/327* (2013.01); *C07C 7/005* (2013.01); *C07C 7/09* (2013.01)

(58) Field of Classification Search
CPC .............. C07C 5/32; C07C 5/327; C07C 7/11

USPC .......................................................... 585/655
See application file for complete search history.

(56) References Cited

U.S. PATENT DOCUMENTS

| | | | |
|---|---|---|---|
| 4,353,794 A | 10/1982 | Winter et al. | |
| 5,276,231 A | 1/1994 | Kocal et al. | |
| 5,300,715 A | 4/1994 | Vora | |
| 5,489,725 A * | 2/1996 | Minkkinen | B01J 8/0285 585/324 |
| 5,849,979 A * | 12/1998 | Kalnes | C07C 7/11 585/809 |
| 6,165,368 A | 12/2000 | Zamarripa | |
| 7,687,677 B1 * | 3/2010 | O'Brien | C10G 45/00 585/634 |
| 2004/0182750 A1 | 9/2004 | Khanna et al. | |
| 2005/0234278 A1 * | 10/2005 | van Egmond | F25J 3/04157 585/324 |

(Continued)

FOREIGN PATENT DOCUMENTS

| | | |
|---|---|---|
| CA | 2415064 A1 | 6/2004 |
| WO | 2014167473 A1 | 10/2014 |

OTHER PUBLICATIONS

Search Report dated Feb. 9, 2017 for corresponding PCT Appl. No. PCT/US2016/058870.

*Primary Examiner* — Philip Y Louie
*Assistant Examiner* — Aaron W Pierpont

(57) ABSTRACT

A process is presented for the removal or aromatics from a hydrocarbon stream. The hydrocarbon stream is generated by a dehydrogenation process that generates aromatics. The process includes a two contact cooler system with the first and second contact coolers using different coolants. The second coolant is a non-aromatic hydrocarbon coolant that will absorb aromatics.

12 Claims, 1 Drawing Sheet

(56) References Cited

U.S. PATENT DOCUMENTS

| | | |
|---|---|---|
| 2009/0218255 A1 | 9/2009 | Claude et al. |
| 2010/0249002 A1* | 9/2010 | Machado ............. C10M 105/06 508/433 |
| 2014/0076780 A1* | 3/2014 | Guichard ................ B01J 23/85 208/111.3 |
| 2014/0200381 A1* | 7/2014 | Josch ........................ C07C 7/05 585/621 |
| 2014/0223960 A1* | 8/2014 | Alekseev ............... F25J 3/0486 62/644 |

* cited by examiner

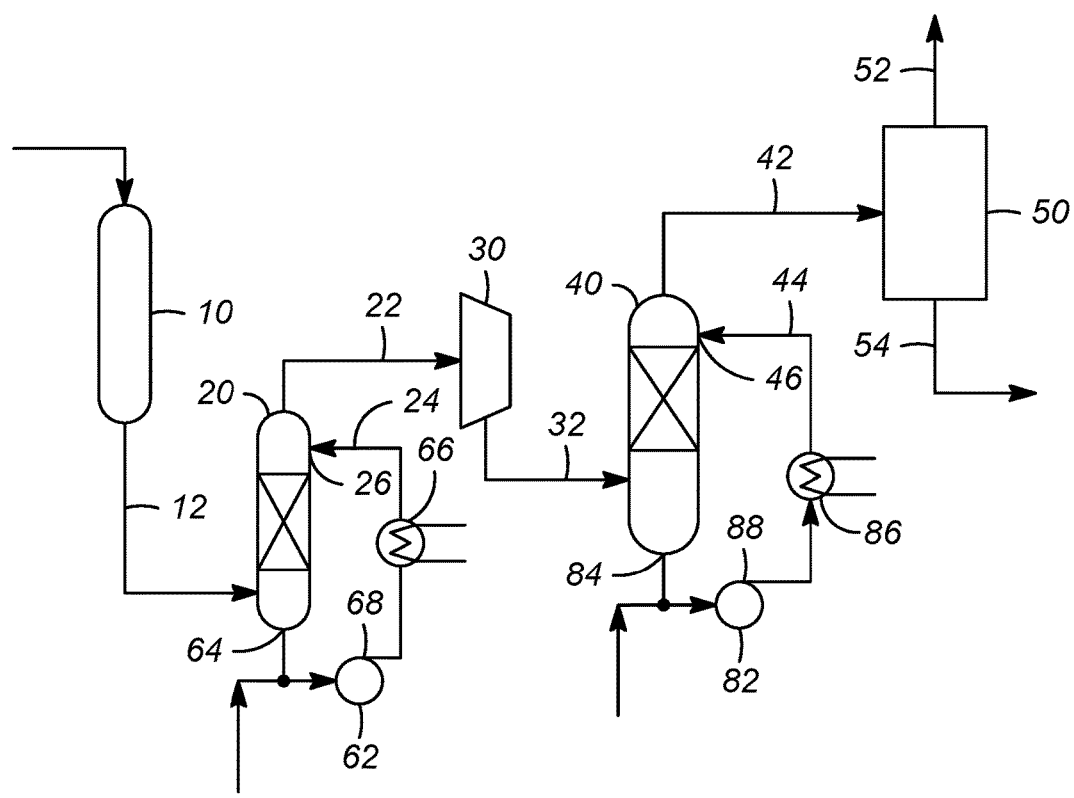

REACTOR EFFLUENT WASH TO REMOVE AROMATICS

CROSS-REFERENCE TO RELATED APPLICATIONS

This application is a Continuation of copending International Application No. PCT/US2016/058870 filed Oct. 26, 2016 which application claims benefit of U.S. Provisional Application No. 62/252,160 filed Nov. 6, 2015, the contents of which cited applications are hereby incorporated by reference in their entirety.

FIELD OF THE INVENTION

The present invention is related to the removal of aromatics from a hydrocarbon process stream.

BACKGROUND

The production of olefins is an important process in the generation of monomers for the manufacture of polymers, detergents and alkylate. The process of generating olefins also generates aromatic compounds. A typical aromatics removal process is shown in U.S. Pat. No. 5,276,231 wherein the aromatics are removed by contact with a solvent.

In another process, in U.S. Pat. No. 5,300,715, a selective aromatics removal zone is used for the adsorption of aromatics onto a sorbent. The sorbent undergoes periodic regeneration for reuse.

In yet another process, in U.S. Pat. No. 6,165,368, a process for the removal of aromatics is presented using an absorbing medium to remove contaminants. The absorbing medium comprise a heavy oil or typical refinery stream having a boiling point between 150° C. to 430° C.

SUMMARY

A process is presented for reducing the aromatics content in a hydrocarbon stream to very low levels.

A first embodiment of the invention is a process for removing aromatics from a process stream, comprising passing the process stream comprising paraffins, olefins and trace aromatics to a first contact cooler using a first coolant to generate a first stream; passing the first stream to a compressor to generate a second stream; and passing the compressed stream to a second contact cooler using a second coolant to generate a third stream comprising olefins and paraffins. An embodiment of the invention is one, any or all of prior embodiments in this paragraph up through the first embodiment in this paragraph further comprising passing a hydrocarbon stream comprising paraffins to a dehydrogenation reactor to generate the process stream comprising olefins and paraffins. An embodiment of the invention is one, any or all of prior embodiments in this paragraph up through the first embodiment in this paragraph further comprising passing the third stream to a cryogenic separation unit to generate an olefin and paraffin product stream. An embodiment of the invention is one, any or all of prior embodiments in this paragraph up through the first embodiment in this paragraph wherein the first coolant comprises an aromatic solvent as a coolant. An embodiment of the invention is one, any or all of prior embodiments in this paragraph up through the first embodiment in this paragraph wherein the second coolant comprises a paraffinic solvent or an alkylate solvent. An embodiment of the invention is one, any or all of prior embodiments in this paragraph up through the first embodiment in this paragraph wherein the first stream is cooled to a temperature between 10° C. and 45° C. An embodiment of the invention is one, any or all of prior embodiments in this paragraph up through the first embodiment in this paragraph wherein the first stream is compressed to a pressure between 250 kPa and 600 kPa. An embodiment of the invention is one, any or all of prior embodiments in this paragraph up through the first embodiment in this paragraph wherein the first stream has a reduced aromatics content. An embodiment of the invention is one, any or all of prior embodiments in this paragraph up through the first embodiment in this paragraph wherein the first stream has an aromatics content below 1500 ppmw. An embodiment of the invention is one, any or all of prior embodiments in this paragraph up through the first embodiment in this paragraph wherein the third stream has an aromatics content below 100 ppmw. An embodiment of the invention is one, any or all of prior embodiments in this paragraph up through the first embodiment in this paragraph wherein the third stream is cooled to a temperature between 10° C. and 45° C.

A second embodiment of the invention is a process for the production of olefins from paraffins, comprising passing a hydrocarbon stream comprising paraffins to a dehydrogenation reactor to generate a dehydrogenation process stream comprising paraffins, olefins and aromatics; passing the dehydrogenation stream to a first contact cooler, wherein the contact cooler uses an aromatic solvent for cooling the dehydrogenation stream to generate a cooled dehydrogenation stream with reduced aromatics; passing the dehydrogenation stream with reduced aromatics to a compressor to generate a compressed stream; passing the compressed stream to a second contact cooler, wherein the contact cooler uses a second solvent for cooling the compressed stream to generate a cooled compressed stream; and passing the cooled compressed stream to a cryogenic separation unit to generate a product stream comprising olefins and paraffins. An embodiment of the invention is one, any or all of prior embodiments in this paragraph up through the second embodiment in this paragraph wherein the second coolant comprises a paraffinic solvent or an alkylate solvent. An embodiment of the invention is one, any or all of prior embodiments in this paragraph up through the second embodiment in this paragraph wherein the first stream is cooled to a temperature between 10° C. and 45° C. An embodiment of the invention is one, any or all of prior embodiments in this paragraph up through the second embodiment in this paragraph wherein the dehydrogenation stream with reduced aromatics is compressed to a pressure between 700 kPa and 1200 kPa. An embodiment of the invention is one, any or all of prior embodiments in this paragraph up through the second embodiment in this paragraph wherein the cooled compressed stream has an aromatics content below 100 ppmw.

A third embodiment of the invention is an apparatus for removing aromatics from a hydrocarbon stream comprising a first contact cooler having a process stream inlet, a process stream outlet, a coolant inlet and a coolant outlet; a first circulating coolant comprising an aromatic solvent within the first contact cooler; a compressor having an inlet in fluid communication with the process stream outlet, and a compressor outlet; a second contact cooler having a process stream inlet in fluid communication with the compressor outlet, a process stream outlet, a coolant inlet and a coolant outlet; and a second circulating coolant comprising a paraffinic or alkylate solvent disposed within the second contact cooler. An embodiment of the invention is one, any or all of prior embodiments in this paragraph up through the third embodiment in this paragraph further comprising a first pump having an inlet in fluid communication with the first contact cooler coolant outlet, and a first pump outlet; a first heat exchanger having an inlet in fluid communication with the first pump outlet, and an outlet in fluid communication with the first contact cooler coolant inlet. An embodiment of the invention is one, any or all of prior embodiments in this paragraph up through the third embodiment in this paragraph further comprising a second pump having an inlet in fluid communication with the second contact cooler coolant outlet, and a second pump outlet; a second heat exchanger having an inlet in fluid communication with the second pump outlet, and an outlet in fluid communication with the second contact cooler coolant inlet. An embodiment of the invention is one, any or all of prior embodiments in this paragraph up through the third embodiment in this paragraph further comprising a cryogenic separation unit.

Other objects, advantages and applications of the present invention will become apparent to those skilled in the art from the following detailed description and drawings.

BRIEF DESCRIPTION OF THE DRAWING

The FIGURE is the process flow of the present invention for removal of aromatics from a process stream comprising olefins.

DETAILED DESCRIPTION

The production of olefins is an important source of building blocks for a variety of products, including polymers, detergents and alkylate. One method is the dehydrogenation of paraffins to generate olefins having the same carbon number as the paraffins. Dehydrogenation is performed at high temperatures, and one of the byproducts is the production of a small amount of aromatic compounds. The aromatic compounds can be detrimental to downstream processes and equipment. The removal of these byproducts improves the product quality and reduces unwanted side reactions. One example is the operation of a sulfuric acid alkylation unit. The presence of a small amount of aromatics can lead to the formation of an emulsion and the loss of product through an increase in the amount of waste to be either reprocessed or otherwise disposed.

The present invention removes the small amounts of aromatics generated by the dehydrogenation process. Purity is important for the quality of the product downstream. The prior art presents methods of removing aromatics, but in order to improve the quality additional removal of trace amounts of aromatics is needed. The present invention allows for removal of trace amounts of aromatics while overcoming limitations due to equilibrium, by using a first absorbent stream that absorbs the bulk of aromatics in the hydrocarbon stream, and a second and different absorbent stream that has little or no aromatics in the second absorbent stream.

The second absorbent stream is an alkylate, or another paraffinic solvent, used in the second contact cooler as the final wash will absorb the heavier aromatic compounds, allowing less aromatics to remain in the vapor phase before it is condensed within the cryogenic unit. Instead of aromatics, equilibrium amount of the paraffinic solvent and Raoult's Law amount of aromatics would remain instead. This would be expected to reduce concentration of aromatics by one or two orders of magnitude to levels at or below 100 ppmw.

The process includes passing a hydrocarbon process stream comprising olefins and aromatics to a first contact cooler using a first coolant. This generates a first stream comprising olefins and some residual aromatics. The first stream is passed to a compressor to generate a second stream that is compressed. The compressed stream is passed to a second contact cooler using a second coolant. This generates a third stream comprising olefins.

The process includes a first coolant that readily absorbs aromatics. The first coolant can comprise an aromatic solvent made up of aromatic compounds and preferably having higher boiling points than the aromatic compounds in the hydrocarbon process stream. When the first stream is cooled with a coolant comprising aromatics, the cooled first stream will have a reduced aromatics content, and preferably have a reduced aromatics content to below 1500 ppm by weight.

The process also includes a second coolant that absorbs aromatics. The second coolant comprises a hydrocarbon mixture having a relatively low aromatics content, or having no aromatics. The second solvent is comprised of higher boiling point hydrocarbons and preferably comprises a paraffinic solvent or an alkylate solvent. The second stream is cooled with a non-aromatics stream and the coolant will be chosen to absorb aromatics. The resulting third stream will preferably have an aromatics content below 100 ppmw.

The process can further include passing the third stream to a cryogenic separation unit to separate low boiling point gases from the third stream and to generate the olefin product stream.

In one embodiment, the process includes passing a hydrocarbon stream comprising paraffins to a dehydrogenation reactor to generate the hydrocarbon stream comprising olefins.

The process conditions include cooling the first stream to a temperature between 10° C. and 45° C. The cooled first stream is compressed to a pressure between 250 kPa and 1200 kPa. The amount of compression is dependent upon the makeup of the hydrocarbon stream. In one embodiment, the first stream is compressed to a pressure between 250 kPa and 600 kPa, and in another embodiment, the first stream is compressed to a pressure between 700 kPa and 1200 kPa. These are gauge pressures. This heats up the first process stream which then is subsequently further cooled to a temperature between 10° C. and 45° C.

The process can be seen in the FIGURE as follows. A process stream 12 is generated by a dehydrogenation reactor 10 to generate a dehydrogenation stream 12. The dehydrogenation stream 12 comprises paraffins, olefins and aromatics. The dehydrogenation stream 12 is passed to a first contact cooler 20, where dehydrogenation stream 12 is contacted with an aromatic solvent 24 for cooling the dehydrogenation stream 12 and generates a cooled dehydrogenation stream 22 with reduced aromatics. The cooled dehydrogenation stream 22 is compressed with a compressor 30 to generate a compressed stream 32. The compressed stream 32 is passed to a second contact cooler 40, where the compressed stream 32 is contacted with a second solvent 44 to generate a cooled and compressed stream 42. The cooled and compressed stream 42 is passed to a cryogenic separation unit 50 to separate the low boiling point gases 52 and to generate a product stream 54 comprising olefins.

The first solvent 24, or coolant, is an aromatics solvent to remove the bulk of the aromatics from the process stream. The second solvent 44, or second coolant, is a paraffinic solvent or an alkylate solvent for absorbing residual aromatics. The process stream 42 leaving the second contact cooler 40 has an aromatics content reduced to below 100 ppmw.

In one embodiment, the first contact cooler 20 includes a means for circulating and cooling the coolant. The circulating means includes a first pump 62 having in inlet in fluid communication with the first contact cooler 20 coolant outlet 64, and a heat exchanger 66 having an inlet in fluid communication with the pump outlet 68 and a heat exchanger outlet in fluid communication with the coolant inlet 26 to the first contact cooler 20.

This embodiment further includes a means for circulating and cooling the second coolant for the second contact cooler 40. The circulating means includes a second pump 82 having in inlet in fluid communication with the second contact cooler 40 coolant outlet 84, and a heat exchanger 86 having an inlet in fluid communication with the pump outlet 88 and a heat exchanger outlet in fluid communication with the coolant inlet 46 to the second contact cooler 40.

The apparatus can further include a cryogenic separation unit 50. The cryogenic separation unit 50 can be a cold box separation unit that is used for separating light gases from hydrocarbons that condense below 20° C., or near 0° C.

While the invention has been described with what are presently considered the preferred embodiments, it is to be understood that the invention is not limited to the disclosed embodiments, but it is intended to cover various modifications and equivalent arrangements included within the scope of the appended claims.

What is claimed is:

1. A process for removing aromatics from a process stream, comprising:
    passing a hydrocarbon stream comprising paraffins to a dehydrogenation reactor to generate a process stream comprising olefins, paraffins, and aromatics;
    passing the process stream to a first contact cooler, wherein the process stream is contacted with a first coolant to generate a first stream, wherein the first coolant comprises an aromatic solvent;
    passing the first stream to a compressor to generate a second stream; and
    passing the second stream to a second contact cooler, wherein the second stream is contacted with a second coolant to generate a third stream comprising olefins and paraffins,
    wherein the second coolant comprises a paraffinic solvent and wherein an aromatics content of the second coolant is less than an aromatics content of the first coolant.

2. The process of claim 1 further comprising passing the third stream to a cryogenic separation unit to generate a product stream comprising olefins and paraffins.

3. The process of claim 1 wherein a temperature of the first stream is between 10° C. and 45° C. prior to being passed to the compressor.

4. The process of claim 1 wherein the first stream is compressed to a pressure between 250 kPa and 600 kPa.

5. The process of claim 1 wherein the first stream has a reduced aromatics content relative to the process stream.

6. The process of claim 5 wherein the first stream has an aromatics content below 1500 ppmw.

7. The process of claim 1 wherein the third stream has an aromatics content below 100 ppmw.

8. The process of claim 1 wherein a temperature of the third stream is between 10° C. and 45° C.

9. A process for the production of olefins from paraffins, comprising:
    passing a hydrocarbon stream comprising paraffins to a dehydrogenation reactor to generate a dehydrogenation process stream comprising paraffins, olefins, and aromatics;
    passing the dehydrogenation stream to a first contact cooler, wherein the dehydrogenation process stream is contacted with a first coolant comprising an aromatic solvent to cool the dehydrogenation process stream and generate a cooled dehydrogenation stream with a reduced aromatics content relative to the content of aromatics in the dehydrogenation process stream;
    passing the dehydrogenation stream with a reduced aromatics content to a compressor to generate a compressed stream;
    passing the compressed stream to a second contact cooler, wherein the compressed stream is contacted with a second coolant comprising a paraffinic solvent to cool the compressed stream and generate a cooled compressed stream; and
    passing the cooled compressed stream to a cryogenic separation unit to generate a product stream comprising olefins and paraffins,
    wherein an aromatics content of the second coolant is less than an aromatics content of the first coolant.

10. The process of claim 9 wherein a temperature of the cooled dehydrogenation stream is between 10° C. and 45° C. prior to being passed to the compressor.

11. The process of claim 9 wherein the cooled dehydrogenation stream with a reduced aromatics content is compressed to a pressure between 700 kPa and 1200 kPa.

12. The process of claim 9 wherein the cooled compressed stream has an aromatics content below 100 ppmw.

* * * * *